United States Patent [19]

Yamaguchi

[11] Patent Number: 5,127,406
[45] Date of Patent: Jul. 7, 1992

[54] APPARATUS FOR MEASURING CONCENTRATION OF SUBSTANCES IN BLOOD

[75] Inventor: Kazuo Yamaguchi, Tokyo, Japan

[73] Assignee: Nihon Kohden Corporation, Tokyo, Japan

[21] Appl. No.: 450,979

[22] Filed: Dec. 15, 1989

[30] Foreign Application Priority Data

Dec. 19, 1988 [JP] Japan ................. 63-319772

[51] Int. Cl.$^5$ .................. A61B 5/00; G01N 33/00
[52] U.S. Cl. ..................... 128/633; 422/73
[58] Field of Search ............. 422/73; 128/632, 633, 128/637

[56] References Cited

U.S. PATENT DOCUMENTS

| | | | |
|---|---|---|---|
| 4,407,290 | 10/1983 | Wilber | 128/633 |
| 4,446,871 | 5/1984 | Imura | 128/633 |
| 4,694,833 | 9/1987 | Hamaguri | 128/633 |
| 4,773,422 | 9/1988 | Isaacson | 128/633 |
| 4,800,885 | 1/1989 | Johnson | 128/633 |
| 4,863,265 | 9/1989 | Flower et al. | 128/633 X |
| 4,869,253 | 9/1989 | Craig, Jr. et al. | 128/633 |
| 4,869,254 | 9/1989 | Stone et al. | 128/633 |
| 4,883,353 | 11/1989 | Hausman et al. | 128/633 X |

*Primary Examiner*—Robert J. Warden
*Assistant Examiner*—Arlen Soderquist
*Attorney, Agent, or Firm*—Sughrue, Mion, Zinn, Macpeak & Seas

[57] ABSTRACT

An apparatus for non-invasively measuring the concentratiuon of a predetermined substance in blood. Light of first and second wavelengths is emitted through a pulsating living tissue, either alternately of simultaneously. The amounts of light of the first and second wavelengths transmitted through the pulsating living tissue are measured for first and second different thicknesses of the pulsating tissue. A calculation is then carried out to determine the concentration of the predetermined substance based on the detected amounts of light of the first and second wavelengths when the pulsating living tissue has the first thickness, the amounts of light of the first and second wavelengths detected when the pulsating living tissue has the second thickness, and absorption coefficients of the substance and absorption coefficients of water at the first and second wavelengths.

6 Claims, 4 Drawing Sheets

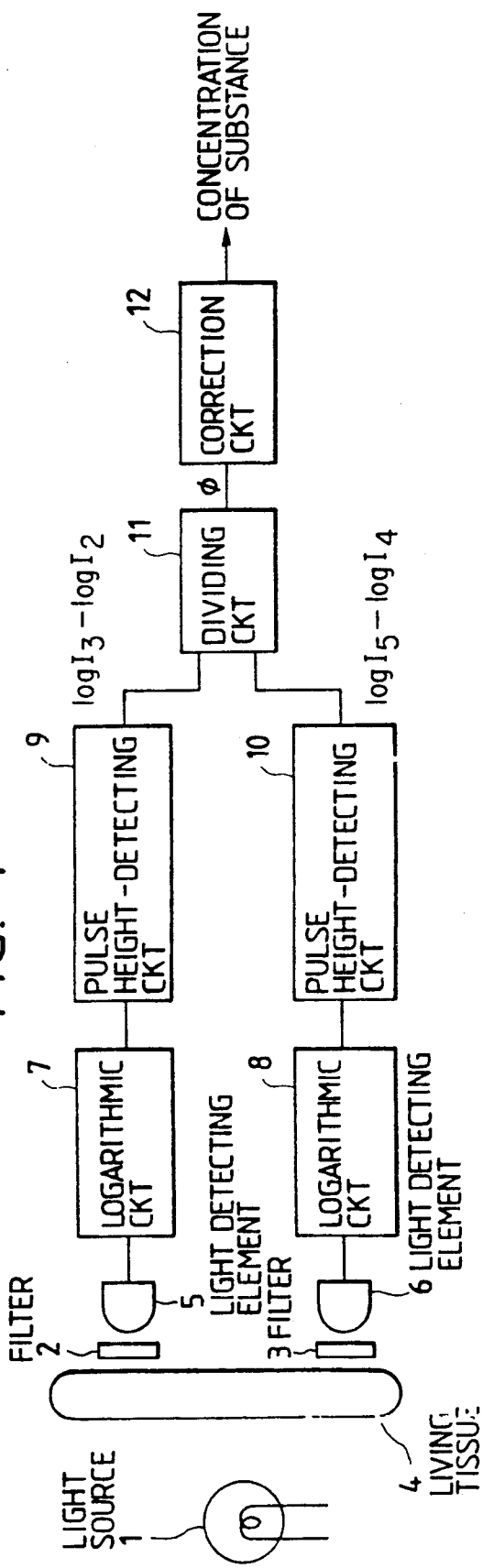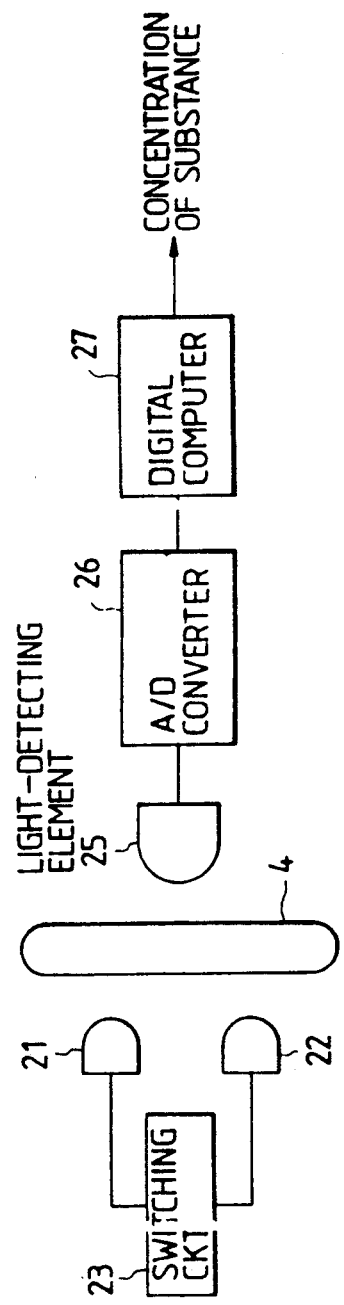

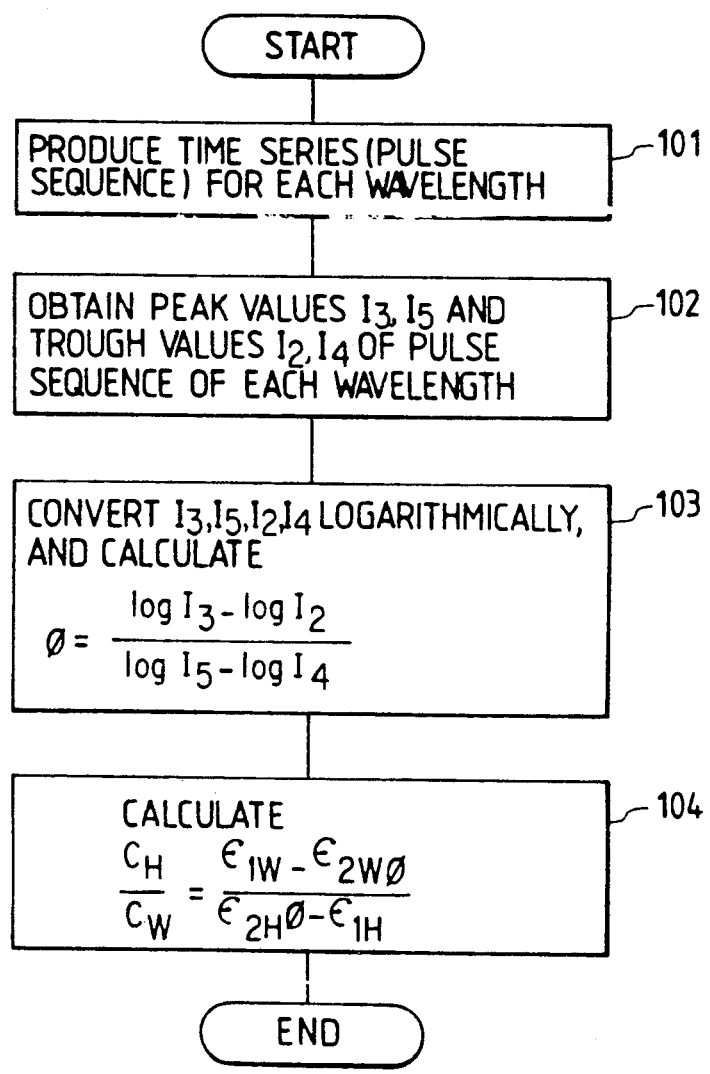

APPARATUS FOR MEASURING CONCENTRATION OF SUBSTANCES IN BLOOD

BACKGROUND OF THE INVENTION

The present invention relates to an apparatus for measuring the concentration of various substances, for example, hemoglobin, bilirubin and the like, in the blood in a living tissue.

Conventionally, the measurement of the concentration of a substance in the blood has been effected invasively. More specifically, a blood sample is collected from the patient, and the thus-collected blood analyzed to measure the concentration of the predetermined substance in question.

With this method, however, it is difficult to frequently conduct the measurement, and each time the measurement is effected, the subject suffers pain.

SUMMARY OF THE INVENTION

The present invention has been made in view of such deficiencies of the prior art, and an object of the invention is to provide an apparatus for measuring the concentration of a predetermined substance in the blood, which apparatus is capable of carrying out the measurement easily and which does not cause pain to the patient.

According to the present invention, there is provided an apparatus for measuring the concentration of a predetermined substance in the blood, comprising:

means for emitting light of first and second wavelengths through a pulsating living tissue;

light detecting means for detecting the amounts of light of first and second wavelengths transmitted through the pulsating living tissue; and calculating means for performing a predetermined calculation to determine the concentration of said substance in the blood based on the amounts of light of said first and second wavelengths detected by said light detecting means when said pulsating living tissue has a certain thickness, the amounts of light of said first and second wavelengths detected by said light detecting means when said pulsating living tissue has a thickness different from said certain thickness, and absorption coefficients of said substance and absorption coefficients of water at said first and second wavelengths.

That is, the light detecting means detects the amounts of light of the first and second wavelengths transmitted through the pulsating living tissue. Based on the amounts of light of the first and second wavelengths detected by the light detecting means when the pulsating living tissue has a certain thickness, the amounts of light of the first and second wavelengths detected by the light detecting means when the pulsating living tissue has a thickness different from said certain thickness, and absorption coefficients of the substance and absorption coefficients of water at the first and second wavelengths, the calculating means performs the predetermined calculation so as to determine the concentration of the specific substance in the blood.

BRIEF DESCRIPTION OF THE DRAWINGS

FIG. 1 is a block diagram of a preferred embodiment of the invention;

FIG. 2 is a block diagram of another preferred embodiment;

FIG. 3 is a flow chart illustrative of the operation of the invention;

DESCRIPTION OF THE PREFERRED EMBODIMENTS

First, the principles of preferred embodiments of the invention will now be described.

Figure 4A:
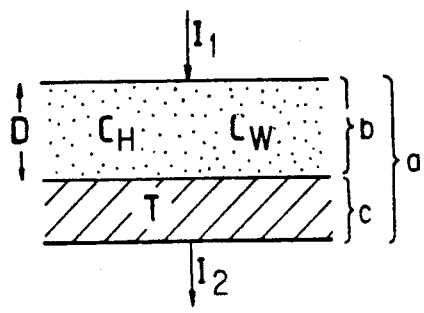
FIGS. 4(a) and 4(b) are diagrams used to illustrate the principles of the present invention.
Figure 4B:
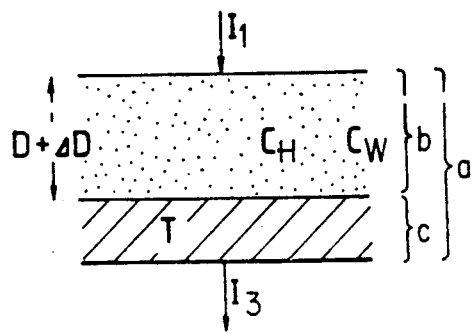

As shown in FIG. 4(a), a living tissue a can be considered as consisting of a blood layer b and another tissue layer c. In general, the thickness of the blood layer b varies with arterial pulsation, but the thickness of the other tissue layer c is constant regardless of the pulsation. Light of a wavelength $\lambda_1$ is applied to the living tissue a. Here, the amount of the incident light is represented by $I_1$, the amount of the light transmitted through the living tissue a is represented by $I_2$ when the thickness of the blood layer b is D as shown in FIG. 4(a), and the amount of the light transmitted through the living tissue a is represented by $I_3$ when the thickness of the blood layer b is $(D+\Delta D)$ as shown in FIG. 4(b). Then, the following relations are established:

$$\log (I_1/I_2) = T + D (\epsilon_{1H}C_H + \epsilon_{1W}C_W) \quad (1)$$

$$\log (I_1/I_3) = T + (D+\Delta D)\cdot(\epsilon_{1H}C_H + \epsilon_{1W}C_W) \quad (2)$$

where T represents the absorbance of the other tissue layer c, $\epsilon_{1H}$ represents the absorption coefficient of a predetermined substance in the blood at the wavelength $\lambda_1$, $\epsilon_{1W}$ represents the absorption coefficient of water at the wavelength $\lambda_1$, $C_W$ represents the amount of water in the blood per unit thickness of the living tissue a, and $C_H$ represents the amount of the predetermined substance in the blood per unit thickness of the living tissue a. Subtracting both sides of formula (2) from both sides of formula (1), the following relation is obtained:

$$\log I_3 - \log I_2 = -\Delta D (\epsilon_{1H}C_H + \epsilon_{1W}C_W) \quad (3)$$

Similarly, light of a wavelength $\lambda_2$ is applied to the living tissue a when its thickness is D, and here the amount of the light transmitted through the living tissue a is represented by $I_4$. Also, light of a wavelength $\lambda_2$ is applied to the living tissue a when its thickness is $(D+\Delta D)$, and here the amount of the light transmitted through the living tissue a is represented by $I_5$. Then, the following formula is established:

$$\log I_5 - \log I_4 = -\Delta D(\epsilon_{2H}C_H + \epsilon_{2W}C_W) \quad (4)$$

where $\epsilon_{2H}$ is the absorption coefficient of the predetermined substance in the blood at the wavelength $\lambda_2$, and $\epsilon_{2W}$ represents the absorption coefficient of water at the wavelength $\lambda_2$.

$$\phi = (\log I_3 - \log I_2)/(\log I_5 - \log I_4) \quad (5)$$

Then, from formulas (3) and (4) above, the following relation is obtained:

$$\phi = (\epsilon_{1H}C_H + \epsilon_{1W}C_2)/(\epsilon_{2H}C_H + \epsilon_{2W}C_W) \quad (6)$$

From formula (6), the following formula is obtained:

$$C_H/C_W = (\epsilon_{1W} - \epsilon_{2W}\phi)/(\epsilon_{2H}\phi - \epsilon_{1H}) \qquad (7)$$

The concentration of the predetermined substance in the blood can be found by determining the value of $(C_H/C_W)$. The reason for this will now be described. Although the concentration of the predetermined substance in the blood is essentially represented by $C_H/C_B$ ($C_B$: the amount of blood per unit thickness of the living tissue a), since blood is mostly composed of water, a good approximation for the concentration of the predetermined substance in the blood is $C_H/C_B = C_H/C_W$.

As indicated by formula (7), if the absorption coefficients $\epsilon_{1W}$ and $\epsilon_{1H}$ of water and the predetermined substance at the wavelength $\lambda_1$, the absorption coefficients $\epsilon_{2W}$ and $\epsilon_{2H}$ of water and the predetermined substance at the wavelength $\lambda_2$, and $\phi$ are determined, then $C_H/C_W$ can be found. $\epsilon_{1W}$, $\epsilon_{1H}$, $\epsilon_{2W}$ and $\epsilon_{2H}$ are constants which do not depend on the patient, and $\phi$ is found by measuring the amounts of light of the wavelengths $\lambda_1$ and $\lambda_2$ transmitted through the living tissue of the patient and then by calculating using formula (5). In other words, in accordance with the present invention, a light detector detects $I_2$ to $I_5$, and a calculating unit calculates $\phi$ from $I_2$ to $I_5$ and further calculates $(\epsilon_{1W} - \epsilon_{2W}\phi)/(\epsilon_{2H}\phi - \epsilon_{1H})$.

If the wavelength $\lambda_1$ is a wavelength at which the absorption coefficient of the predetermined substance is much higher than the absorption coefficient of water, and the wavelength $\lambda_2$ is a wavelength at which the absorption coefficient of water is much higher than the absorption coefficient of the predetermined substance, then formula (7) can be replaced by the following:

$$C_H/C_W \approx (\epsilon_{2W}/\epsilon_{1H})\phi \qquad (8)$$

Figure 5:
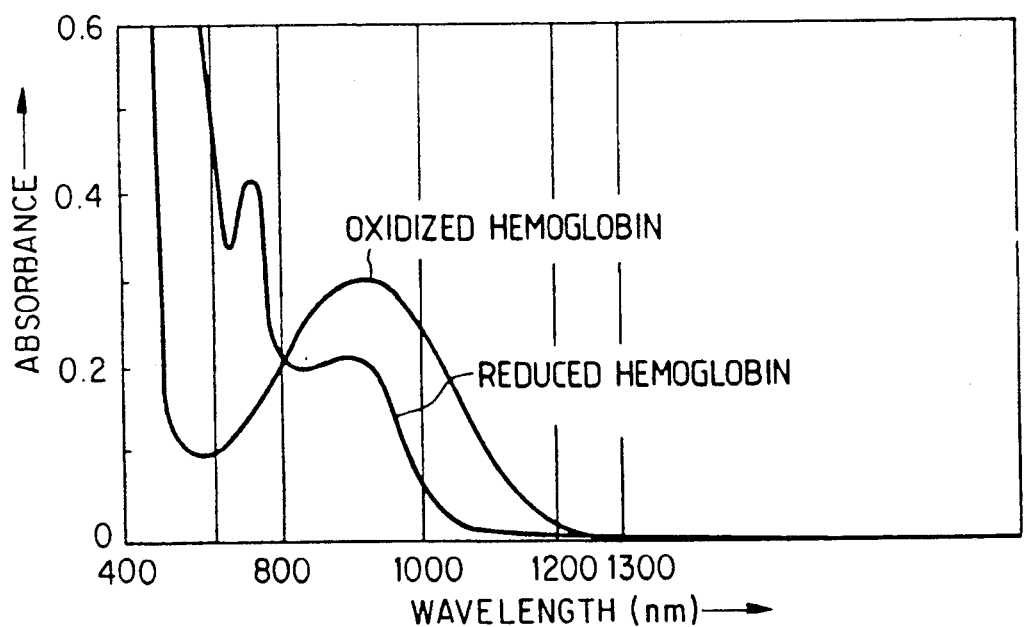
FIG. 5 is an illustration showing the relation between absorbance of hemoglobin and wavelength by way of example.
Figure 6:
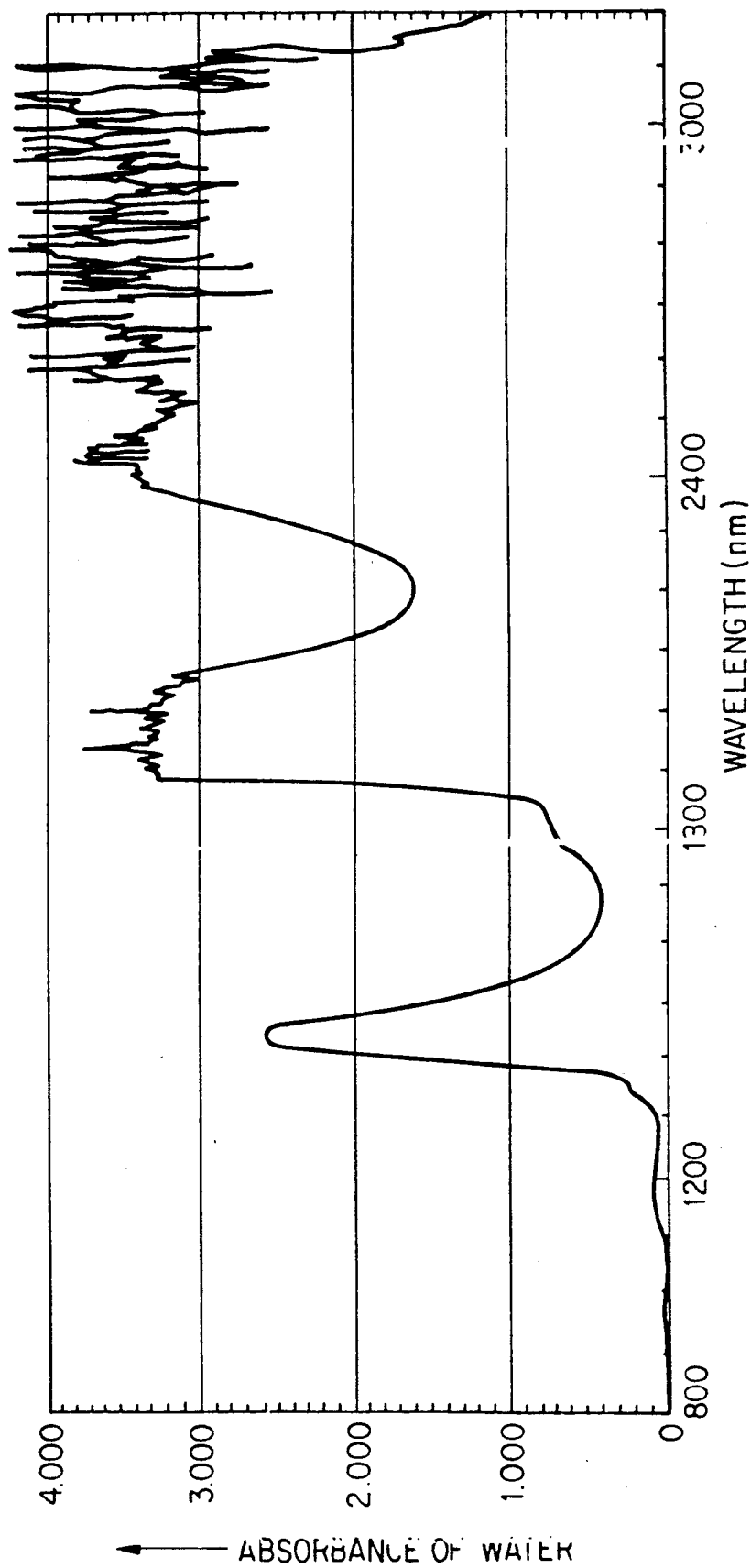
FIG. 6 is an illustration showing the relation between absorbance of water and the wavelength.

FIG. 5 shows the relation between wavelength and the absorbance of hemoglobin, which is typical of the substances in the blood which can be measured with the use of the invention, and FIG. 6 shows the relation between the absorbance of water and wavelength.

Next, based on the above principles, the invention will be described in more detail.

FIG. 1 is a block diagram of a preferred embodiment of an apparatus of the present invention. In this figure, reference numeral 1 denotes a light source. Filters 2 and 3 are positioned so as to receive light from the light source 1 via the living tissue 4. The filter 2 allows only light rays of a wavelength $\lambda_1$, which are absorbed to a much greater extent by the predetermined substance present in the blood than water, to pass therethrough. The filter 3 allows only light rays of a wavelength $\lambda_2$, which are absorbed to a much greater extent by water than the predetermined substance present in the blood, to pass therethrough. It is preferred that the filter 2 allow the passage of light of a wavelength of 805 nm at which the absorption coefficient of oxidized hemoglobin is the same as the absorption coefficient of reduced hemoglobin. Light-detecting elements 5 and 6 receive light rays passed respectively through the filters 2 and 3, and output electrical signals corresponding to the amounts of light received thereby. The outputs of the light-detecting elements 5 and 6 are fed respectively to pulse height-detecting circuits 9 and 10 via logarithmic circuits 7 and 8. Each of the pulse height-detecting circuits 9 and 10 outputs a signal representing the difference between the peak of a pulsating component of the output of a respective one of the logarithmic circuits 7 and 8 and the trough of the pulsating component. A dividing circuit 11 provides a signal representing the ratio between the outputs of the pulse height-detecting circuits 9 and 10. A correction circuit 12 multiplies the output of the dividing circuit 11 by a predetermined factor. In this embodiment, the light source 1, the filters 2 and 3, and the light-detecting elements 5 and 6 constitute a light detecting unit, and the logarithmic circuits 7 and 8, the pulse height-detecting circuits 9 and 10, the dividing circuit 11, and the correction circuit 12 constitute a calculating unit.

Next, the operation of the apparatus of the above construction will be described.

First, the living tissue 4 is interposed between the light source 1 and the filters 2 and 3. Preferably, the living tissue 4 is, for example, that of an ear lobe or finger. The light-detecting element 5 receives only light rays of the wavelength $\lambda_1$ from the light transmitted or passed through the living tissue 4, and outputs to the logarithmic circuit 7 an electrical signal corresponding to the amount of light thus received. Similarly, the light-detecting element 6 receives only light rays of the wavelength $\lambda_2$ from the light transmitted through the living tissue 4, and outputs to the logarithmic circuit 8 an electrical signal corresponding to the amount of light thus received. The logarithmic circuits 7 and 8 provide logarithms of the outputs of the light-detecting elements 5 and 6, respectively, and output these to the pulse height-detecting circuits 9 and 10, respectively. Each of the pulse height-detecting circuits 9 and 10 provides the difference between the peak and trough of the pulsating component of the output of a respective one of the logarithmic circuits 7 and 8, and outputs an electrical signal corresponding to this difference.

It is assumed that the peak value of the thickness of the living tissue 4 pulsating is $D + \Delta D$, and that the trough value is D. When the thickness of the living tissue 4 is D, the light-detecting element 5 outputs a signal representative of the light amount $I_2$, as shown in FIG. 4(a). When the thickness of the living tissue 4 is $D + \Delta D$, the light-detecting element 5 outputs a signal representative of the light amount $I_3$, as shown in FIG. 4(b). At these times, in accordance with the outputs of the light-emitting element 5, the logarithmic circuit 7 correspondingly outputs a signal representative of log $I_2$ and a signal representative of log $I_3$. Therefore, the pulse height-detecting circuit 9 outputs a signal representative of the difference (log $I_3$ − log $I_2$) between the peak value and trough value of the signal output from the logarithmic circuit 7. Similarly, when the thickness of the living tissue 4 is D, the light-detecting element 6 outputs signal representative of the light amount $I_4$. When the thickness of the living tissue 4 is $D + \Delta D$, the light-detecting element 6 outputs a signal representative of the light amount $I_5$. At these times, in accordance with the outputs of the light-emitting element 6, the logarithmic circuit 8 correspondingly outputs a signal representative of log $I_4$ and a signal representative of log $I_5$. Therefore, the pulse height-detecting circuit 10 outputs a signal representative of the difference (log $I_5$ − log $I_4$) between the peak value and trough value of the signal output from the logarithmic circuit 8.

The dividing circuit 11 calculates the ratio between the outputs of the pulse height-detecting circuits 9 and 10, that is, the dividing circuit evaluates the formula (5), $\phi = (log\ I_3 - log\ I_2)/(log\ I_5 - log\ I_4)$, and outputs the result to the correction circuit 12. The correction circuit 12 evaluates the formula (8), $C_H/C_W=(\epsilon_2 w \epsilon_1 H)\phi$, using the calculation result ($\phi$) determined by the dividing circuit 11, and outputs its calculation result to a display device or a recording device (not shown).

In this embodiment, as described above, the wavelength $\lambda_1$ is a wavelength at which the absorption coefficient of the predetermined substance present in the blood, is much higher than the absorption coefficient of water and the wavelength $\lambda_2$ is a wavelength at which the absorption coefficient of water is much higher than the absorption coefficient of predetermined substance. Therefore, the apparatus can be constructed using circuits which perform simple calculations.

FIG. 2 shows a block diagram of another preferred embodiment of the invention. In this figure, reference numerals 21 and 22 denote light-emitting diodes (LED). The light-emitting diode 21 emits light of a wavelength $\lambda_1$, whereas the light-emitting diode 22 emits light of wavelength $\lambda_2$. The light-emitting diodes 21 and 22 are connected to a switching circuit 23 so that these two diodes are alternately lit. The light rays emitted from the light-emitting diodes 21 and 22 are received by a light-detecting element 25 via the living tissue 4. The light-detecting element 25 outputs an electrical signal corresponding to the light amount received by it. An analog-to-digital (A/D) converter 26 converts the output of the light-detecting element 25 into digital form. A digital computer 27 processes the output of the A/D converter 26 in accordance with a flow chart shown in FIG. 3. In this embodiment, the light-emitting diodes 21 and 22, the switching circuit 23, and the light-detecting element 25 constitute a light detecting unit, and the A/D converter 26 and the digital computer 27 constitute a calculating unit.

Next, the operation of this embodiment will be described.

First, the living tissue 4 is interposed between the light-emitting diodes 21 and 22 and the light-detecting element 25. The light-detecting element 25 alternately receives light of a wavelength $\lambda_1$ emitted from the light-emitting diode 21 and light of a wavelength $\lambda_2$ emitted from the light-emitting diode 22, and outputs to the A/D converter 26 signals corresponding to the thus received light. The A/D converter 26 converts the output of the light-detecting element 25 into digital form, and outputs it to the digital computer 27.

The digital computer 27 performs the processing shown in FIG. 3. First, in Step 101, with respect to each of the light of wavelengths $\lambda_1$ and $\lambda_2$, a time series of the amount of light received by the light-detecting element 26 is produced. More specifically, pulses of the light of wavelengths $\lambda_1$ and $\lambda_2$ transmitted through the living tissue 4 are produced. Next, in Step 102, the peak values $I_3$ and $I_5$ of the wavelengths $\lambda_1$ and $\lambda_2$ as well as the trough values $I_2$ and $I_4$ thereof are detected. In Step 103, these values are logarithmically converted, and $\phi$ is determined using the formula, $\phi=(log\ I_3-log\ I_2)/(log\ I_5-log\ I_4)$. Next, Step 104 is processed using $\epsilon_{1H}$, $\epsilon_{1W}$, $\epsilon_{2H}$, $\epsilon_{2W}/\epsilon_{1H}$ and $\epsilon_{1W}$ are respectively the absorption coefficients of the predetermined substance and water at the wavelength $\lambda_1$, and $\epsilon_{2H}$ and $\epsilon_{2W}$ are respectively the absorption coefficients of the predetermined substance and water at the wavelength $\lambda_2$. In step 104 which are stored beforehand as well as $\phi$ obtained in Step 103, the concentration of the predetermined substance is determined through calculation of the formula $(C_H/C_W)=(\epsilon_1 w-\epsilon_2 w\phi)/(\epsilon_2 H\phi-\epsilon_1 H)$, and the result is outputted to a display device or a recording device (not shown).

In this embodiment, the two wavelengths $\lambda_1$ and $\lambda_2$ may be any wavelengths in so far as the two are not identical. Therefore, the light-emitting diodes 21 and 22 may be any types in so far as the two emit light of different wavelengths. This facilitate the construction of the light detecting unit.

In the present invention, the concentration of the predetermined substance in the blood ca be measured in a non-invasive manner. Therefore, the measurement can be frequently carried out without causing pain to the patient. Therefore, for example, with respect to hemoglobin, the apparatus of the present invention is very useful for medical examination to determine and diagnose anemia in infants and children and for carrying out such diagnosis in the home.

What is claimed is:

1. An apparatus for measuring the concentration of a predetermined substance present in blood, comprising:
   means for emitting light of first and second wavelengths through a pulsating living tissue;
   light detecting means for detecting amounts of said light of said first and second wavelengths transmitted through said pulsating living tissue; and
   calculating means for that determines a concentration of said predetermined substance based on amounts of light of said first and second wavelengths detected by said light detecting means when said pulsating living tissue has a first thickness, amounts of light of said first and second wavelengths detected by said light detecting means when said pulsating living tissue has a second thickness different from said first thickness, and absorption coefficients of said substance and absorption coefficients of water at said first and second wavelengths, wherein said first wavelength is a wavelength at which an absorption coefficient of said substance present in said blood is higher than the absorption coefficient of water, and said second wavelength is a wavelength at which an absorption coefficient of water is higher than the absorption coefficient of said substance.

2. The apparatus of claim 1, wherein said light emitting means comprises means emitting light of substantially 805 nm as said first wavelength.

3. The apparatus of claim 1, wherein said light emitting means comprises means for emitting said light of said first and second wavelengths simultaneously, and said light detecting means comprises means for separately and simultaneously detecting amounts of said light of said first and second wavelengths transmitted through said pulsating living tissue.

4. The apparatus of claim 1, wherein said light detecting means comprises first and second filters passing light of said first and second wavelengths, respectively, and first and second light detectors receiving light through said first and second filters, respectively.

5. The apparatus of claim 1, wherein said light emitting means comprises means for emitting said light of said first and second wavelengths in alternating sequence.

6. The apparatus of claim 1, wherein said calculating means determines the concentration of said predetermined substance based on:

$$C_H/C_W \simeq (\epsilon_1 w - \epsilon_2 w\phi)/(\epsilon_2 H\phi - \epsilon_1 H).$$

where, $$\phi = (\log I_3 - \log I_2)/(\log I_5 - \log I_4), \text{ and}$$

$C_W$ is an amount of water in the blood per unit thickness of said living tissue, $C_H$ is an amount of said substance in said blood per unit thickness of said living tissue, $\epsilon_{1H}$ is an absorption coefficient of said predetermined substance in aid blood at said first wavelength, $\epsilon_{1W}$ is an absorption coefficient of water at said first wavelength, $\epsilon_{2H}$ is an absorption coefficient of said predetermined substance in said blood at said second wavelength, $\epsilon_{2W}$ is an absorption coefficient of water at said second wavelength, $I_2$ is an amount of light of said first wavelength transmitted through said living tissue when said thickness of said blood layer is said first thickness, $I_3$ is an amount of light of said first wavelength transmitted through said living tissue when said thickness of said blood layer is said second thickness, $I_4$ is an amount of light of said second wavelength transmitted through said living tissue when said thickness of said blood layer is said first thickness, and $I_5$ is an amount of light of said second wavelength transmitted through said living tissue when said thickness of said blood layer is said second thickness.

* * * * *